US009101357B2

(12) United States Patent
Regner

(10) Patent No.: US 9,101,357 B2
(45) Date of Patent: Aug. 11, 2015

(54) PHYSIOLOGIC ABDOMINAL CLOSURE

(75) Inventor: Justin L. Regner, North Little Rock, AR (US)

(73) Assignee: Board of Trustees of the University of Arkansas, Little Rock, AR (US)

( * ) Notice: Subject to any disclaimer, the term of this patent is extended or adjusted under 35 U.S.C. 154(b) by 1859 days.

(21) Appl. No.: 11/811,260

(22) Filed: Jun. 8, 2007

(65) Prior Publication Data

US 2008/0306496 A1    Dec. 11, 2008

(51) Int. Cl.
*A61B 17/04*     (2006.01)
*A61B 17/064*    (2006.01)
*A61B 17/06*     (2006.01)

(52) U.S. Cl.
CPC ......... *A61B 17/0643* (2013.01); *A61B 17/0401* (2013.01); *A61B 2017/0496* (2013.01); *A61B 2017/06104* (2013.01)

(58) Field of Classification Search
CPC ........... A61B 17/0643; A61B 17/0401; A61B 2017/00584; A61B 2017/00588; A61B 2017/00606; A61B 2017/0496; A61B 2017/0601; A61B 2017/0081; A61B 2017/0083
USPC ......... 606/213, 215, 216, 218, 219, 220, 221, 606/142, 151
See application file for complete search history.

(56) References Cited

U.S. PATENT DOCUMENTS

| | | | |
|---|---|---|---|
| 1,209,083 A * | 12/1916 | Wagner | 119/866 |
| 3,977,397 A | 8/1976 | Kalnberz et al. | |
| 4,730,615 A * | 3/1988 | Sutherland et al. | 606/215 |
| 5,005,266 A * | 4/1991 | Fister et al. | 24/601.5 |
| 5,100,418 A * | 3/1992 | Yoon et al. | 606/139 |
| 5,437,683 A | 8/1995 | Neumann et al. | |
| 5,972,022 A * | 10/1999 | Huxel | 606/215 |
| 5,976,159 A * | 11/1999 | Bolduc et al. | 606/142 |
| 6,074,401 A | 6/2000 | Gardinier et al. | |
| 6,254,615 B1 * | 7/2001 | Bolduc et al. | 606/142 |
| 6,648,844 B2 * | 11/2003 | Kamerman | 602/36 |
| 6,936,037 B2 | 8/2005 | Bubb et al. | |
| 6,951,553 B2 | 10/2005 | Bubb et al. | |
| 6,994,702 B1 | 2/2006 | Johnson | |
| 7,004,915 B2 | 2/2006 | Boynton et al. | |

(Continued)

OTHER PUBLICATIONS

International Preliminary Report on Patentability, PCT/US08/03921, Dec. 11, 2009.

(Continued)

*Primary Examiner* — Alexander Orkin
(74) *Attorney, Agent, or Firm* — Richard Blakely Glasgow

(57) ABSTRACT

A closure device and method to close the abdomen between surgical procedures and maintain a normal physiologic tension on the fascia to prevent undue retraction. In one embodiment, the closure device includes a "needled carabiner" attached to a rubberband of specific tension. The rubberband mimics the physiologic tension the abdominal wall normally experiences during daily activities and allows the abdominal compartment to expand as needed to maintain a healthy intra-abdominal pressure. The bands contract to maintain the intra-abdominal pressure and slowly pull the abdominal fascia back to the midline to facilitate surgical closure of the abdomen. In one embodiment, the "needled carabiner" includes a hinged surgical needle with a protected cap. The hinged needle is placed outside the normal suture line, thereby limiting the amount of surgical trauma the fascia endures. The strength of the rubberbands may be varied to accommodate differently sized individuals.

7 Claims, 10 Drawing Sheets

(56) References Cited

U.S. PATENT DOCUMENTS

| | | |
|---|---|---|
| 7,108,683 B2 | 9/2006 | Zamierowski |
| 7,351,250 B2 | 4/2008 | Zamierowski |
| 7,381,211 B2 | 6/2008 | Zamierowski |
| 7,381,859 B2 | 6/2008 | Hunt et al. |
| 2002/0029063 A1 | 3/2002 | Wittmann |
| 2002/0042606 A1 | 4/2002 | Castaneda et al. |
| 2003/0114865 A1* | 6/2003 | Sater .............................. 606/151 |
| 2003/0130694 A1 | 7/2003 | Bojarski et al. |
| 2004/0044364 A1 | 3/2004 | Devries et al. |
| 2004/0176783 A1* | 9/2004 | Edoga et al. ................... 606/139 |
| 2004/0186489 A1* | 9/2004 | Lee ................ 606/153 |
| 2005/0059984 A1* | 3/2005 | Chanduszko et al. ......... 606/151 |
| 2005/0229367 A1* | 10/2005 | Thompson ................... 24/599.9 |
| 2005/0273066 A1 | 12/2005 | Wittmann |
| 2006/0052821 A1* | 3/2006 | Abbott et al. ................. 606/213 |
| 2006/0147492 A1 | 7/2006 | Hunter et al. |
| 2007/0049942 A1* | 3/2007 | Hindrichs et al. ............... 606/72 |
| 2007/0250115 A1* | 10/2007 | Opolski et al. ................. 606/215 |

OTHER PUBLICATIONS

Malbrain, M., et al., Results from the International Conference on Intra-abdominal Hypertension and Abdominal Compartment Syndrome. I. Definitions, Intensive Care Med., vol. 32, pp. 1722-1732, available on-line as early as Jul. 27, 2006.

Cheatham, M., et al., Results from the International Conference on Intra-abdominal Hypertension and Abdominal Compartment Syndrome. II. Recommendations, Intensive Care Med., not paginated, available on-line as early as Feb. 21, 2007.

Cothren, C., et al., One hundred percent fascial approximation with sequential abdominal closure of the open abdomen, The American Journal of Surgery, vol. 192, pp. 238-242, available on-line Jul. 21, 2006.

Fantus, R., et al., Use of controlled fascial tension and an adhesion preventing barrier to achieve delayed primary fascial closure in patients managed with an open abdomen, The American Journal of Surgery, vol. 192, pp. 243-247, available on-line Jul. 21, 2006.

Wittman, D., The Use of the Artificial Bur (Wittmann PatchTM), http://www.openabdomen.org/3-OP-Techn&Bur/OPT-long.html, 9 pages, date of publication unknown.

Star Surgical-Wittmann Patch Instructions, http://www.starsurgical.com/instructions.html, Starsurgical, Inc., 4 pages, date of publication unknown.

International Search Report and Written Opinion of International Searching Authority, PCT/US08/03921, Jul. 25, 2008.

* cited by examiner

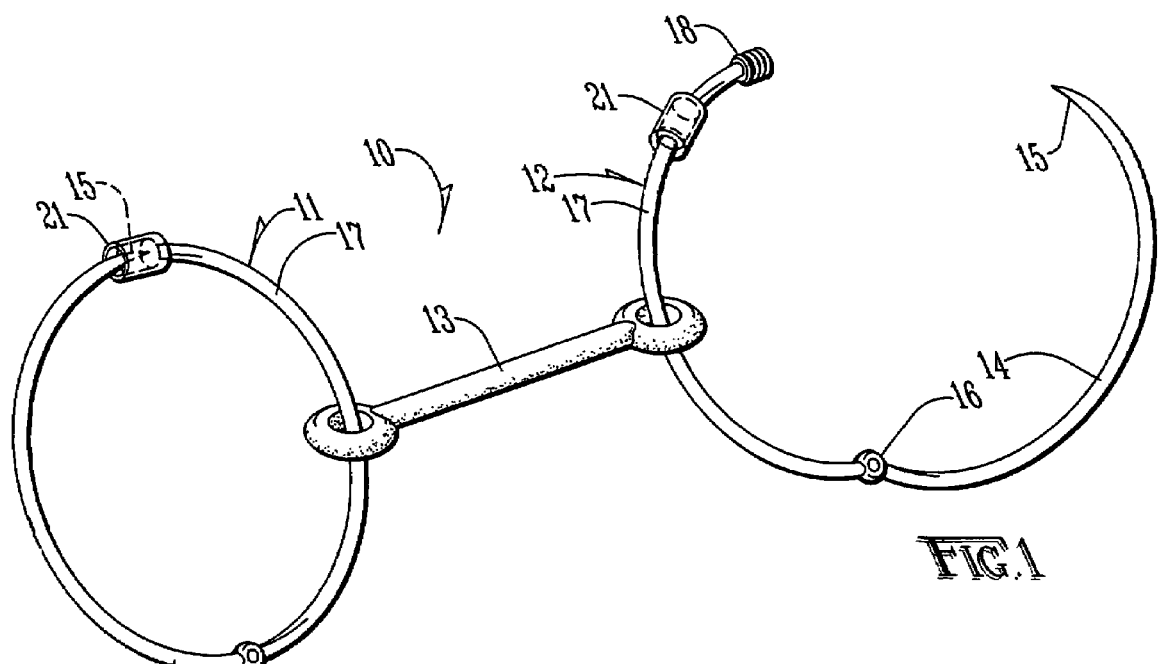
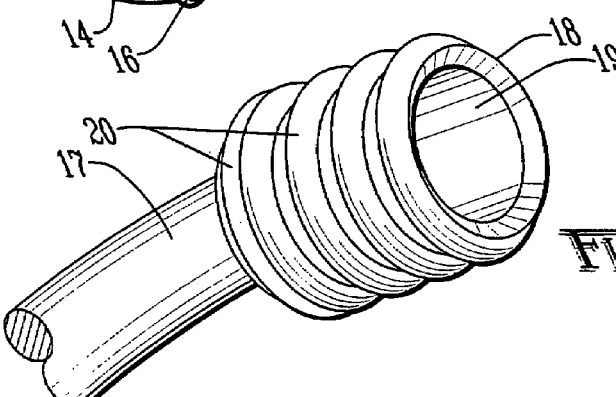
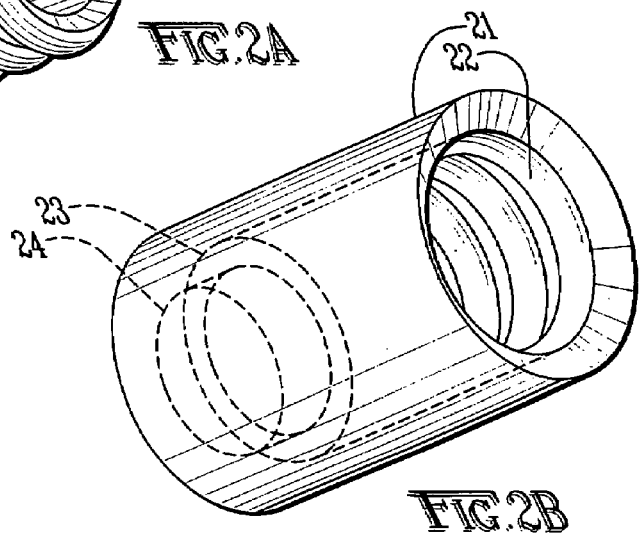
FIG.1
FIG.2A
FIG.2B

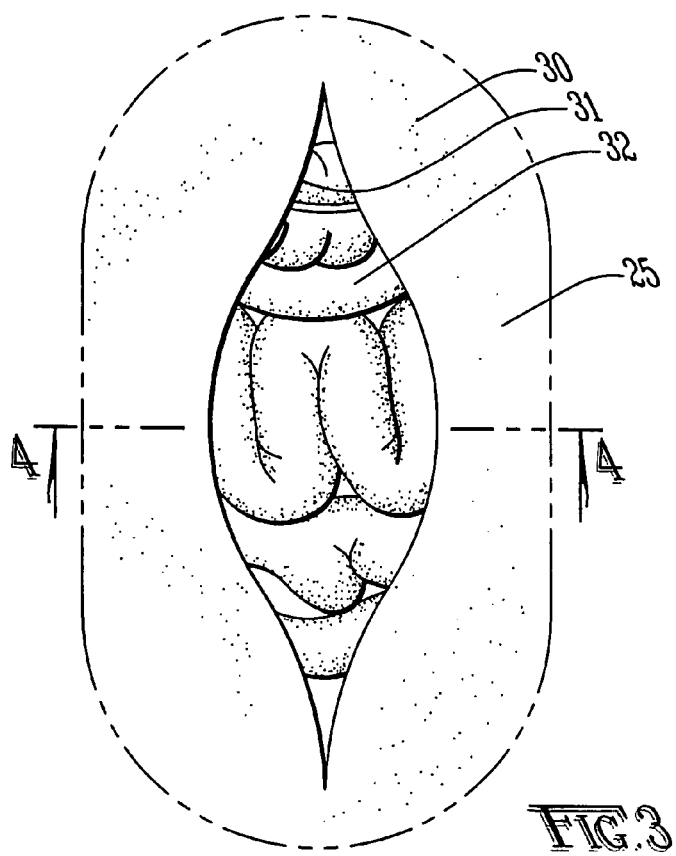
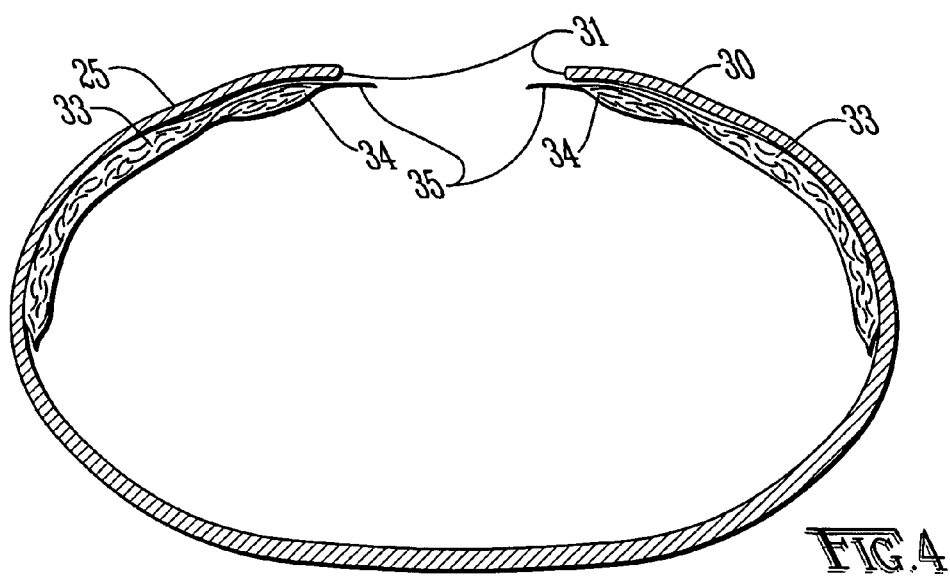

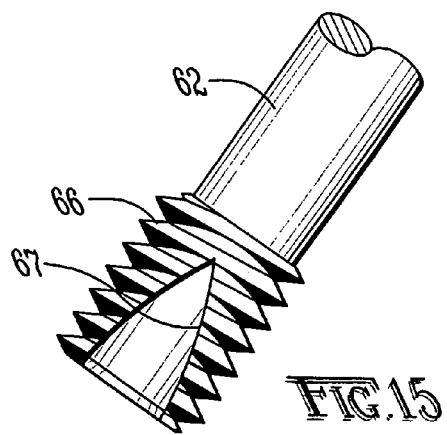
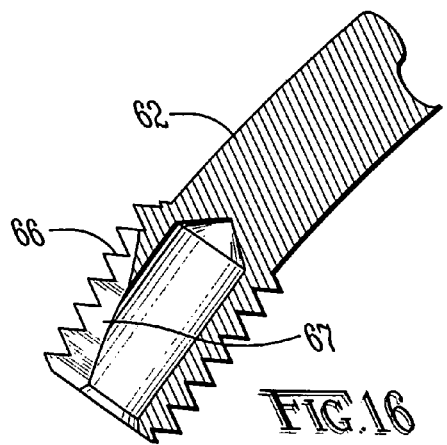
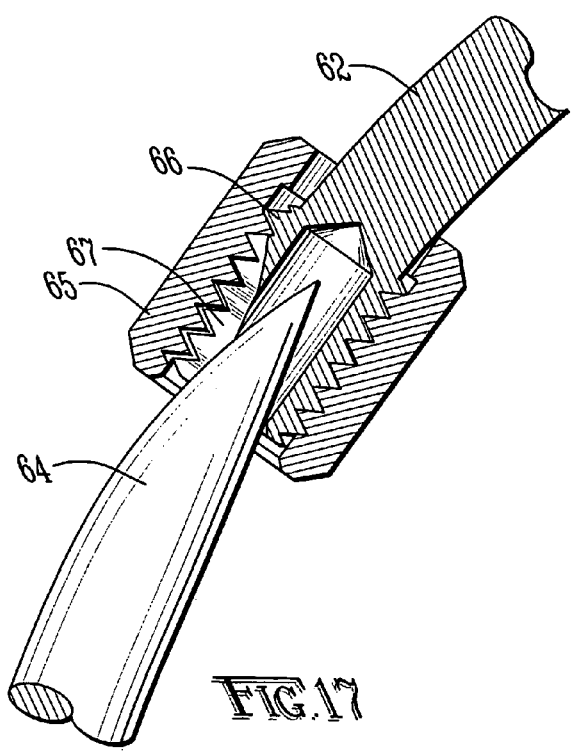

PHYSIOLOGIC ABDOMINAL CLOSURE

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

1. Field of the Invention

The present invention relates to devices for temporarily closing the abdomen between open surgical procedures.

2. Brief Description of the Related Art

After abdominal trauma, abdominal compartment syndrome scenarios, pediatric abdominal malformations, or major open abdominal procedures, surgeons leave the abdomen "packed" open, which allows the abdomen to decompress. During this time, the fascia (sheets of fibrous connective tissue enveloping, separating or binding together muscles, organs and other structures) and the muscles retract and pull apart, preventing future primary surgical closure of the fascia and necessitating various surgical procedures to close the abdomen or repair the hernia at a later date.

The limitations of the prior art are overcome by the present invention as described below.

BRIEF SUMMARY OF THE INVENTION

The present invention is a closure device to temporarily close and stabilize the abdomen between surgical procedures and maintain a normal physiologic tension on the fascia to prevent undue retraction. The closure device incorporates a pair of "needled carabiners" attached to either end of tensioning means, including in one embodiment a rubberband of specific tension. The term "carabiner" is borrowed from the terminology of mountaineering where the term refers to a ring with a spring catch used for fastening ropes. Although the "needled carabiner" of the present invention does not operate in the same fashion, its appearance is suggestive of the mountaineering "carabiner." It is not intended, however, that the use of the term limits in any way the scope of the present invention as described herein.

The "needled carabiner" comprises a surgical needle portion hinged to a locking portion with a securing element. The securing element prevents injury to surgical staff, nursing and the patient from the needle tip and locks the needle into a closed position. The needled carabiner allows a one-time placement of the closure device into muscle tissue outside the normal suture line, thereby limiting the amount of surgical trauma the fascia endures. Limiting the trauma increases the strength of a future surgical closure of the abdomen and prevents recurrent incisional hernias.

In one embodiment, rubberbands of specific tension mimic the physiologic tension the abdominal wall normally experiences during daily activities. During times of stress, the tension of the rubberbands allows the abdominal compartment to expand as needed to maintain a healthy intra-abdominal pressure of 15 mm Hg or less. As swelling decreases, the rubberbands contract to maintain the intra-abdominal pressure and slowly pull the abdominal fascia back to the midline to facilitate surgical closure of the abdomen. The present invention is not limited to rubberbands, but may use other tensioning means such as springs or other tensioning devices known to those of ordinary skill in the art.

The strength of the rubberbands may be varied to accommodate different abdominal pressures of differently sized individuals. For example, various sizes and strengths of rubberbands may be employed based on the patient's height and/or waist circumference. The rubberbands may also be interchangeable to accommodate various degrees of abdominal expansion based on the patient's disease process.

The closure device of the present invention prevents fascial trauma from repeated operations, allows the abdomen to expand as needed to prevent renal, pulmonary, hepatic and cardiac failure, and provides specific tension to slowly approximate the fascia once the inflammatory process has resolved.

The closure device may also be used with chronic open abdominal wounds, chronic pressure sores, and fasciotomy sites. The closure device may be used with known wound vacuum systems to decrease wound closure times, such as V.A.C.® Abdominal Dressing, available from KCI Licensing, Inc.

These and other features, objects and advantages of the present invention will become better understood from a consideration of the following detailed description of the preferred embodiments and appended claims in conjunction with the drawings as described following:

BRIEF DESCRIPTION OF THE SEVERAL VIEWS OF THE DRAWINGS

FIG. 1 is a front elevation view of one embodiment of the closure device of the present invention showing one needled carabiner in the closed, locked and protective position and one needled carabiner in the open position.

FIG. 2A is a partial perspective view of one embodiment of the lock portion of the needled carabiner showing a hollow screw affixed to an end of the lock portion. The hollow screw is shown with external screw threads.

FIG. 2B is a perspective view of a protective cap showing internal screw threads for threadedly advancing the protective cap over the hollow screw of FIG. 2A and an internal flange in the protective cap to limit the distance the cap is able to advance over the hollow screw.

FIG. 3 is a top plan view of the abdomen of a patient showing an open abdominal incision and peritoneal contents.

FIG. 4 is a cross sectional elevation view of the patient and abdominal incision of FIG. 3 along the line 4-4.

FIG. 12 shows the needled carabiner in the open position. FIG. 13 shows the tip of the needle portion received into the screw tip of the lock portion. FIG. 14 shows the protective cap screwed over the needle tip to lock the needle portion.

FIGS. 15-17 are views of the screw tip of FIGS. 12-14. FIG. 15 is a top plan view of the screw tip of FIG. 12 showing a recess for receiving the needle tip. FIG. 16 is a side elevation view of the screw tip in cross section. FIG. 17 is a side elevation of the screw tip in cross section showing the disposition of the needle tip when received into the recess.

DETAILED DESCRIPTION OF THE INVENTION

Figure 2C:
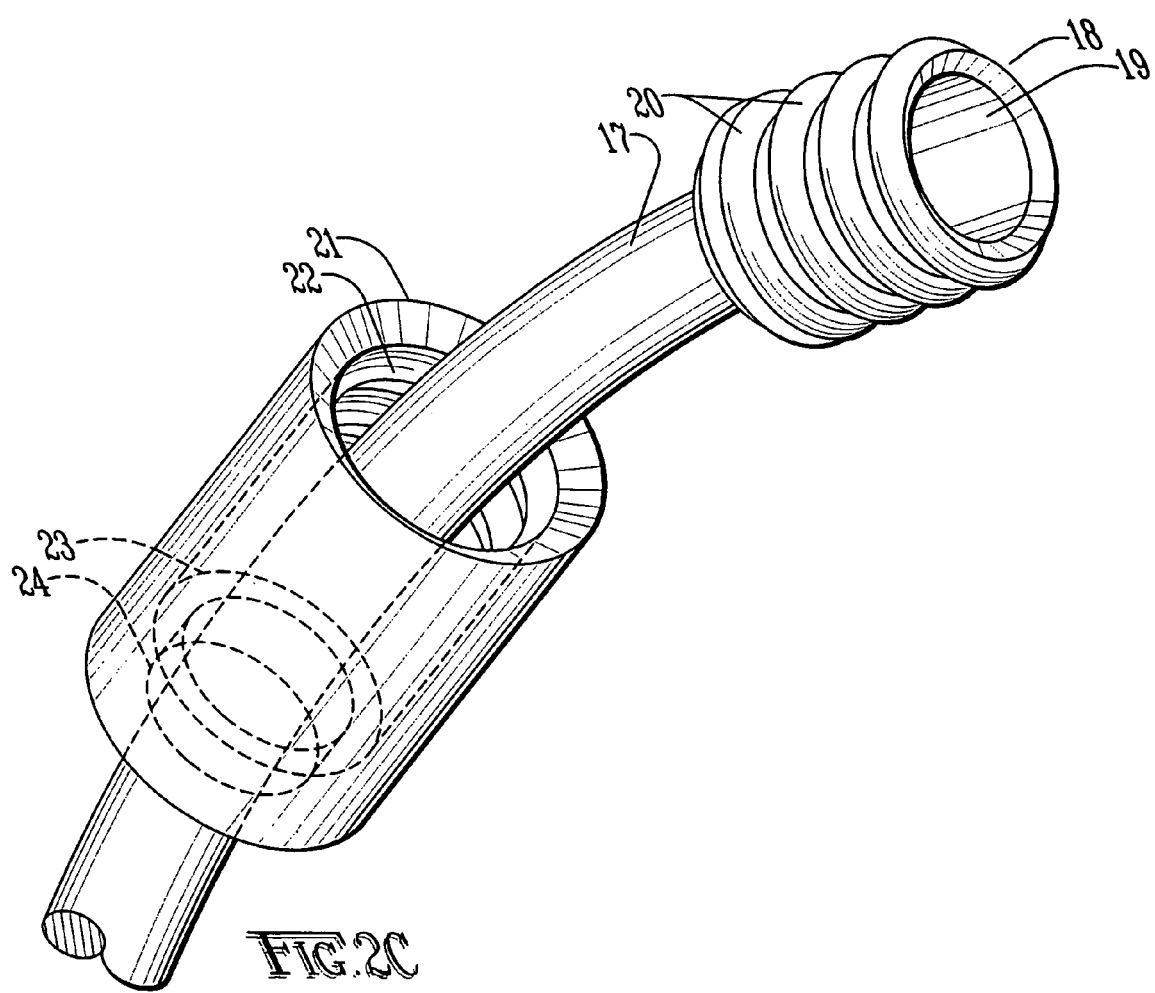
FIG. 2C is a perspective view of the protective cap disposed on the end of the lock portion prior to advancing over the hollow screw.

With reference to FIGS. 1-17, the preferred embodiments of the present invention may be described as follows:

As shown in FIG. 1, the closure device of the present invention comprises two needled carabiners 11, 12 connected to either end of a tensioner for maintaining a desired tension between the two needled carabiners. In the described embodiment, the tensioner is a rubberband 13. Although the invention is described with reference to an embodiment employing a rubberband 13, the present invention is not so limited and may employ other tensioners such as springs or the like, or other tensioning devices known to those of ordinary skill in the art. The rubberband 13 or other tensioner is provided with a specific tension to mimic the physiologic tension the abdominal wall normally experiences during daily activities. During times of stress, the tension of the rubberbands 13 allows the abdominal compartment to expand as needed to maintain a healthy intra-abdominal pressure of 15 mm Hg or less. As swelling decreases, the rubberbands 13 contract to maintain the intra-abdominal pressure and slowly pull the abdominal fascia back to the midline to facilitate surgical closure of the abdomen.

In the embodiment of FIG. 1, one needled carabiner 11 is shown in the closed, locked and protective position and one needled carabiner 12 is shown in the open position. The needled carabiner 11, 12 comprises a needle portion 14 having a first end connected by a hinge 16 to a lock portion 17 and a needle tip 15 at an opposite second end. The lock portion 17 has a first end connected at the hinge 16 to the needle portion 14. A securing element locks the lock portion 17 to the needle portion 14 and desirably provides protection to the needle tip 15 to protect the patient and medical personnel. In the described embodiment, the securing element is hollow screw 18 affixed (for example by spot welding) at an opposite second end of the lock portion 17. Other embodiments of the securing element are described below. The needle portion 14 and the lock portion 17 may conveniently be in the shape of circular arcs but the present invention is not limited to such shapes. For example, and not by way of limitation, the needled carabiners may be triangular or elliptical in outline. The particular shape may be varied as desirable for particular applications or the preferences of the user. Factors that may be significant in determining the shape of the needled carabiners include structural integrity, ease of use, and ease of manufacture.

As shown in the embodiment of FIG. 2A, the hollow screw 18 has a hollow end 19 and external screw threads 20. The hollow end 19 is disposed so as to receive the needle tip 15 of the needle portion 14 when the needle portion 14 is rotated around the hinge 16 into a closed position as shown by needled carabiner 11 in FIG. 1.

With reference to FIGS. 1 and 2A-2C, a protective cap 21 having a central bore 24 is slidably received on lock portion 17 between hollow screw 18 and hinge 16. Protective cap 21 is provided with internal screw threads 22 for being threadedly received onto the external screw threads of hollow screw 18. An internal flange 23 limits how far the protective cap 21 may be advanced over the hollow screw 18. The protective cap 21 is allowed to advance over hollow screw 18 to a sufficient degree that needle tip 15 is prevented from being removed from hollow end 19. Needle tip 15 is thus covered by protective cap 21 to protect the patient and surgical staff from accidental contact. By angling the needle tip 15 with respect to the protective cap 21, when the protective cap 21 is advanced over the hollow screw 18, needle portion 14 is locked into position and cannot be opened with respect to lock portion 17. If the needle portion 14 and the lock portion 17 are in the shape of circular arcs, the appropriate angle may be obtained if the needle portion 14 describes less than ½ of the circular circumference and the lock portion 17 describes greater than ½ of the circular circumference. In the preferred embodiments, the needle portion 14 describes approximately ⅜ of the circular circumference and the lock portion 17 describes approximately ⅝ of the circumference. If the needle portion 14 and the lock portion 17 overlap by at least 3 degrees of radial angle, the needle portion 14 will be locked by advancing the protective cap 21 over the needle tip 15 as shown in FIGS. 12-17. As described below, various other securing elements may be employed either alone or in combination to lock needle portion 14 with respect to lock portion 17 and to protect patients and medical personnel from needle tip 15. For example, the embodiment of FIGS. 9A-9C may be used in combination with the embodiment of FIGS. 1-2C.

The closure device 10 is used in the following manner. The abdomen 30 of a patient is shown with an open abdominal incision 31 revealing the peritoneal contents 32. FIG. 4 is a cross sectional view of the patient and abdominal incision 31 of FIG. 3 along the line 4-4. Also shown is the skin 25 of the patient, the oblique muscle 33, rectus muscle 34, and the linea alba 35. The linea alba 35 is a vertical medial line of tendinous tissue in the abdominal wall formed of fibers covering the rectus muscle 34. The peritoneal contents are not shown in FIG. 4 for the sake of clarity.

Figure 5:
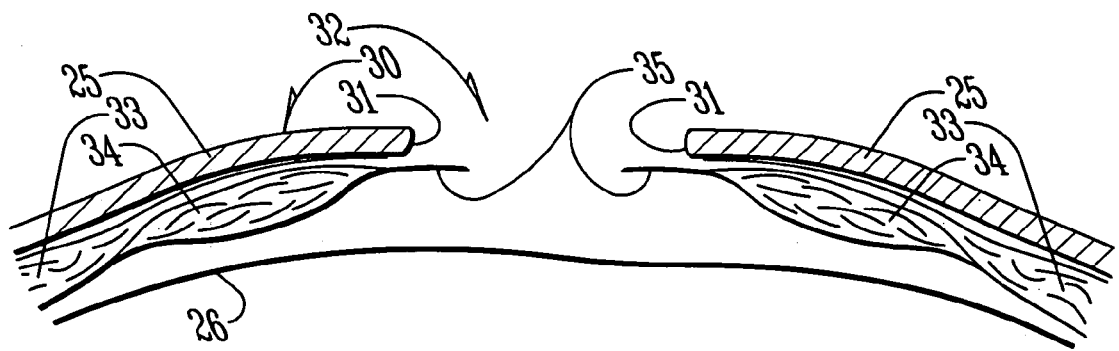
FIG. 5 is a close-up partial view of the incision of FIG. 4 showing a water permeable protective sheet over the peritoneal contents of the patient.
Figure 6:
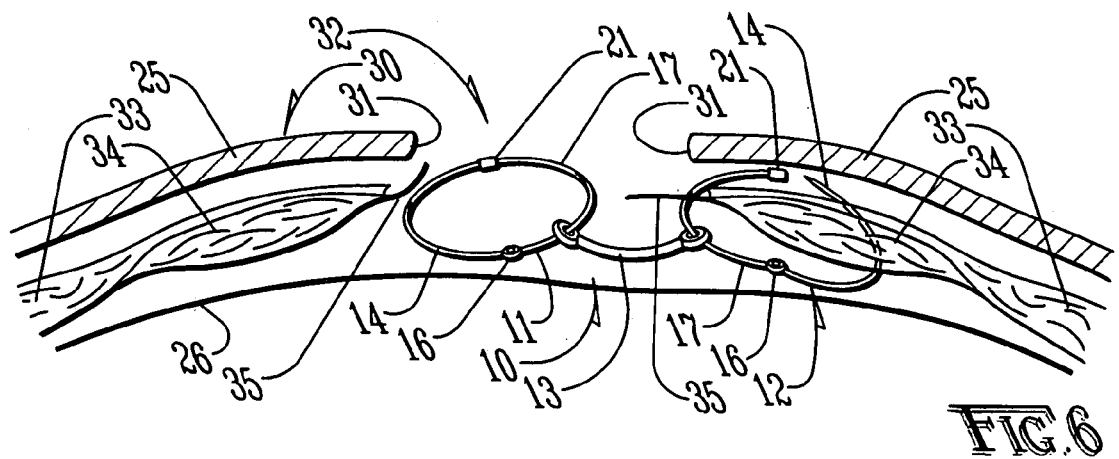
FIG. 6 is the close-up partial view of FIG. 5 showing a closure device of the present invention where a needle portion of one of the needled carabiners is driven through the abdominal rectus muscle on one side of the abdominal incision.
Figure 7:
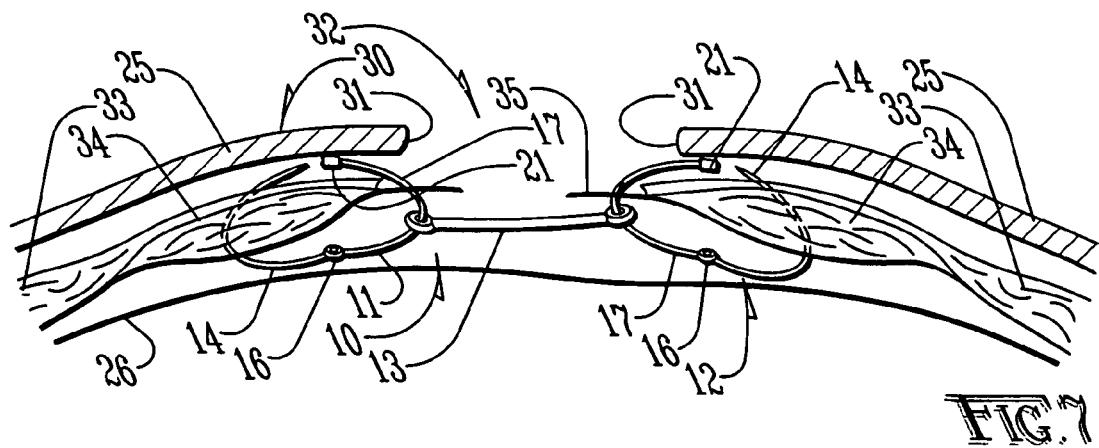
FIG. 7 is the close up partial view of FIG. 5 showing the needle portions of both needled carabiners driven through the respective rectus muscles on respective sides of the abdominal incision.
Figure 8:
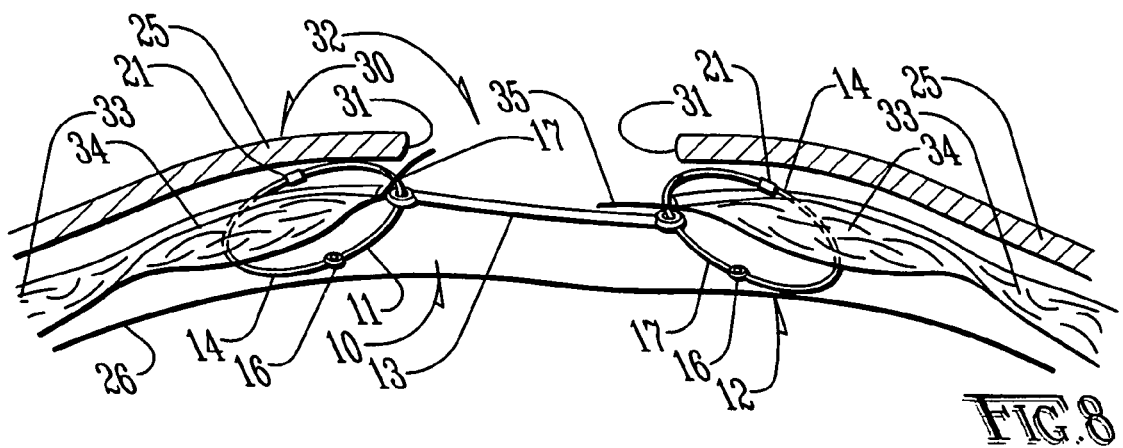
FIG. 8 is the close up partial view of FIG. 5 showing both needled portions locked and protectively capped by the threaded advance of the respective protective caps over the respective hollow screws of the lock portions of the needled carabiners and connected to one another by a rubberband.

As shown in FIG. 5, a water permeable protective sheet 26, preferably polyurethane, is placed to cover the entire peritoneal contents to prevent bowel herniation. FIG. 6 shows a closure device 10. The needle portion 14 of one of the needled carabiners 12 is attached on one side of the abdominal incision 31 away from the normal suture line, preferably by driving the needle portion 14 through the rectus muscle 34 on one side of the abdominal incision 31. As shown in FIG. 7, the needle portion 14 of the other needled carabiner 11 is attached to the opposite side of the abdominal incision 31, preferably by driving the needle portion 14 through the rectus muscle 34 on the opposite side of the abdominal incision 31. Both of the needle portions 14 of the respective needled carabiners 11, 12 are closed as shown in FIG. 8 to secure the respective needle tips 15 which have been received into the hollow ends 19 of the respective hollow screws 18. The respective protective caps 21 are then screwed over the respective hollow screws 18 and over the respective needle tips 15 to secure and lock both needled carabiners 11, 12 as described in more detail below.

Typically four to eight of the closure devices 10 of the present invention will be required depending on the length of the abdominal incision 31 and the size of the patient. When fully deployed, the abdominal contents of the patient are held in place and a physiologic pressure of 15 mm Hg or less is maintained. As swelling subsides, the two sides of the incision 31 are drawn together without damage to the fascia.

The intra-abdominal pressure is the steady state pressure within the abdominal cavity. The elasticity of the abdominal walls and the character of the contents of the abdominal cavity determine the intra-abdominal pressure. It is therefore necessary to take various factors into consideration in determining the appropriate strength of the rubberbands needed to maintain healthy intra-abdominal pressure of less than about 15 mm HG. The size of the individual patient, including the patient's height and the circumference of the abdomen, as well as the length of the incision 31 may affect the selection of the size and strength of the rubberbands 13. The rubberbands 13 may also be interchangeable to accommodate various degrees of abdominal expansion based on the patient's disease process.

The tension of the rubberbands 13 can be estimated for a particular individual by considering the abdomen to be approximately a cylinder (for a slender individual) or a sphere (for an obese individual). The determination of whether the abdomen should be considered a cylinder or sphere may also be affected by such factors as the height of the individual and the length of the incision. The intra-abdominal pressure, P, is therefore approximated by the formula $P=2\pi T/C$ (for a cylinder) or $P=4\pi T/C$ (for a sphere), where T is the tension and C is the circumference. As an example, consider an individual with a 36.0 inch (91.4 cm) waist circumference and a desired intra-abdominal pressure of 10 mm Hg. In this case, the total tension required for a sphere would be 72.8 mm Hg cm and for a cylinder 145.0 mm Hg cm. The total tension would be divided over the number of rubberbands 13 employed for closing a particular incision to estimate an average tension per rubberband. The actual tension of each rubberband 13 would probably vary somewhat from the estimated average value.

The present invention may be used in combination with the known technology of wound vacuums (also known as vacuum-assisted closure), such as V.A.C.® Abdominal Dressing, available from KCI Licensing, Inc., to accelerate healing.

Figure 9A:
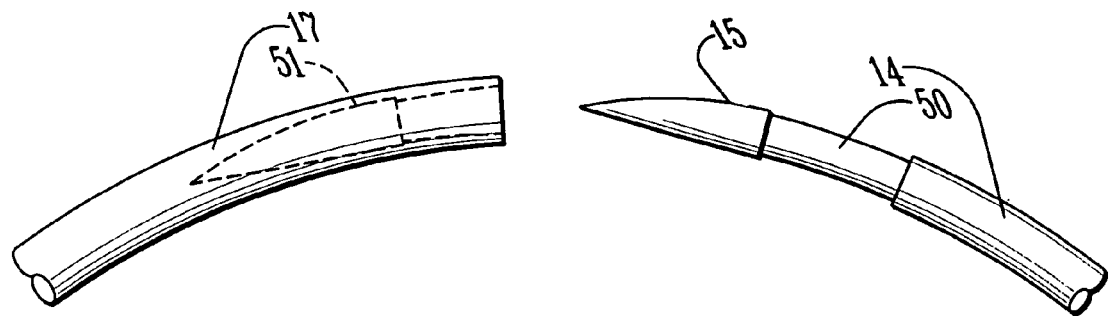
FIG. 9A is a partial exploded bottom plan view of the lock portion and needle portion of an alternative embodiment in which a recess in the needle portion interlocks with a complementary recess in the lock portion.
Figure 9B:
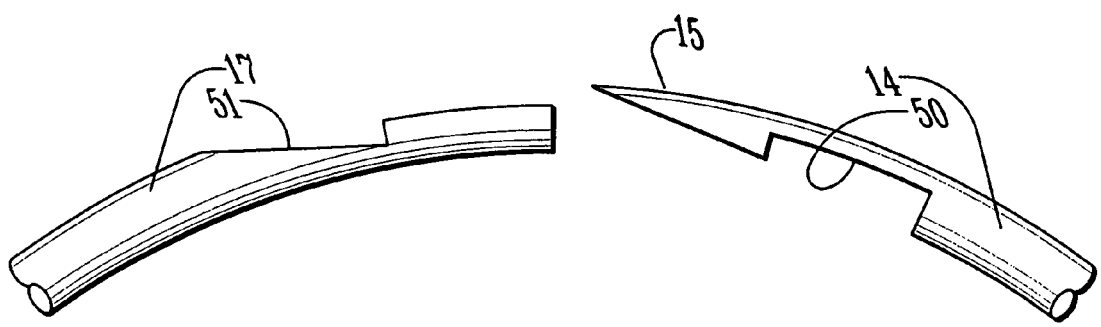
FIG. 9B is a partial exploded side elevation view of the lock portion and needle portion in cross section of the embodiment of FIG. 9A.
Figure 9C:
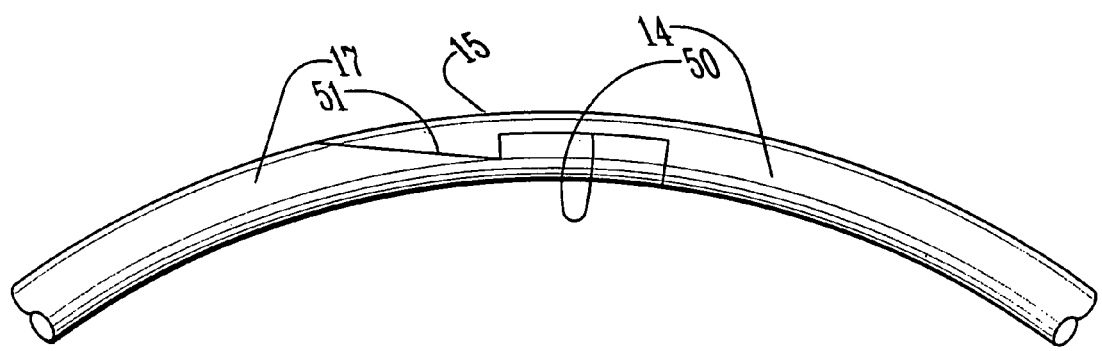
FIG. 9C is a partial side elevation view of the lock portion and needle portion of the embodiment of FIG. 9A showing the lock portion and the needle portion in the interlocked position.

The securing element is further described with reference to FIGS. 9A-9C. In one embodiment, the needle portion 14 is provided with a recess 50 which interlocks with a complementary recess 51 in the lock portion 17. As seen in FIG. 9C, when the needle portion 14 and the lock portion 17 are interlocked, the tip 15 of the needle portion 14 is flush with the surface of the lock portion 17 so as to avoid the dangers of an exposed needle tip. Alternatively, this embodiment may also be provided with threaded sections on needle portion 14 and lock portion 17 and a protective cap as described with reference to FIGS. 2A-C and 10A-C.

Figure 10A:
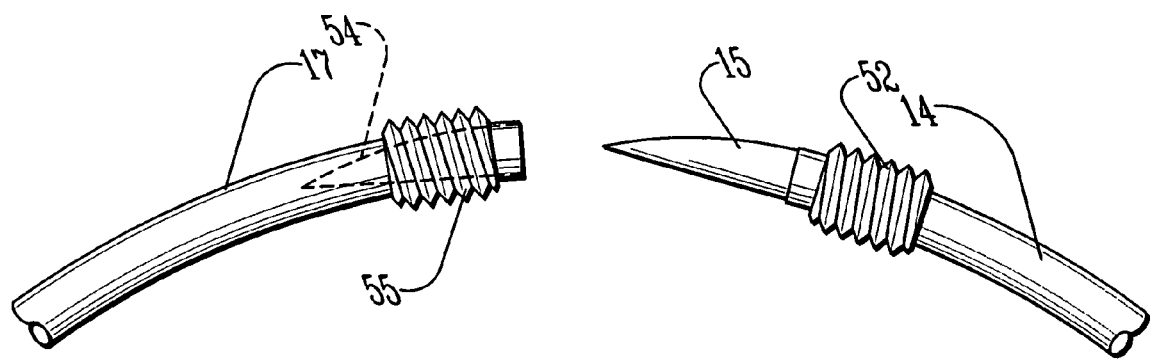
FIG. 10A is a partial exploded side elevation view of the lock portion and needle portion of a further alternative embodiment in which the needle portion is provided with an externally threaded section for threadedly receiving the protective cap.
Figure 10B:
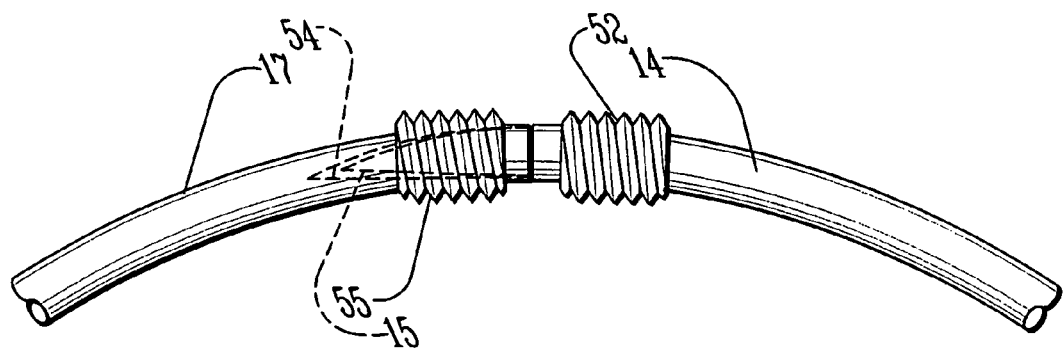
FIG. 10B is a side elevation view of the lock portion and the needle portion in the closed position before the protective cap is advanced over the threaded section of the needle portion.
Figure 10C:
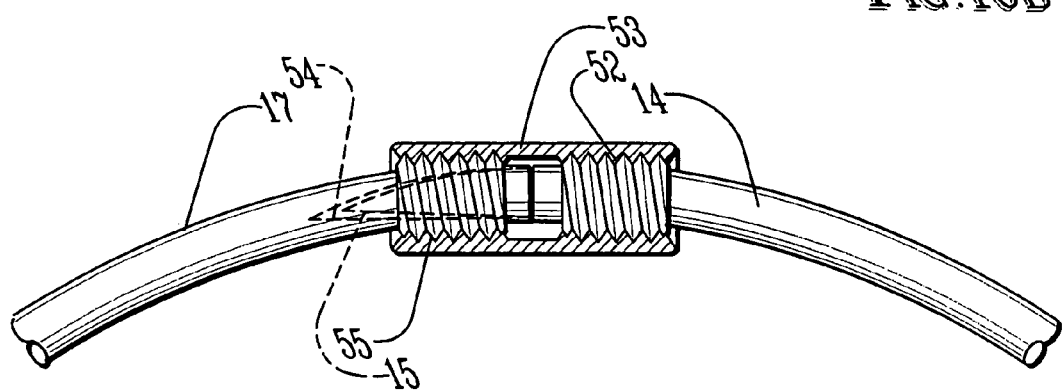
FIG. 10C is a side elevation view in cross section of the alternative embodiment of FIG. 10B in the locked and protective position with the protective cap advanced over the threaded section of the needle portion.

In the further alternative embodiment of FIGS. 10A-C, the needle portion 14 is provided with an externally threaded section 52 for threadedly receiving a protective cap 53 which is provided with internal threads. The lock portion 17 also has a threaded section 55 and a complementary hollow 54 for receiving the tip 15 of the needle portion 14. The protective cap 53 may be threaded over either the lock portion 17 or the needle portion 14. The protective cap may also be provided with a flange as described with respect to FIGS. 2A-C. In order to protect the tip 15 and to lock the needle portion 14 to the lock portion 17, the tip 15 is placed within the complementary hollow 54 and the protective cap 53 is threadedly advanced over the threaded sections 55, 52 as shown in FIG. 10C.

Figure 11A:
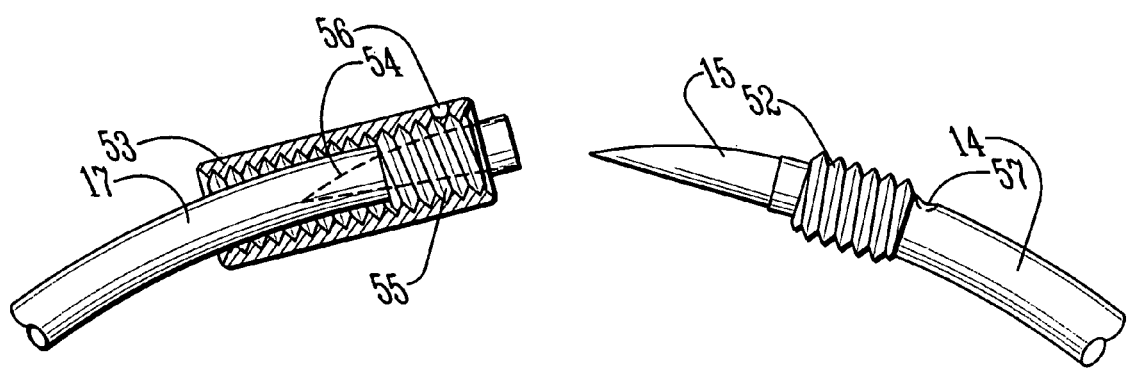
FIG. 11A is an exploded side elevation view in cross section of a still further embodiment of the lock portion and the needle portion showing the lock portion with a spring loaded ball for locking into a complementary socket on the needle portion.
Figure 11B:
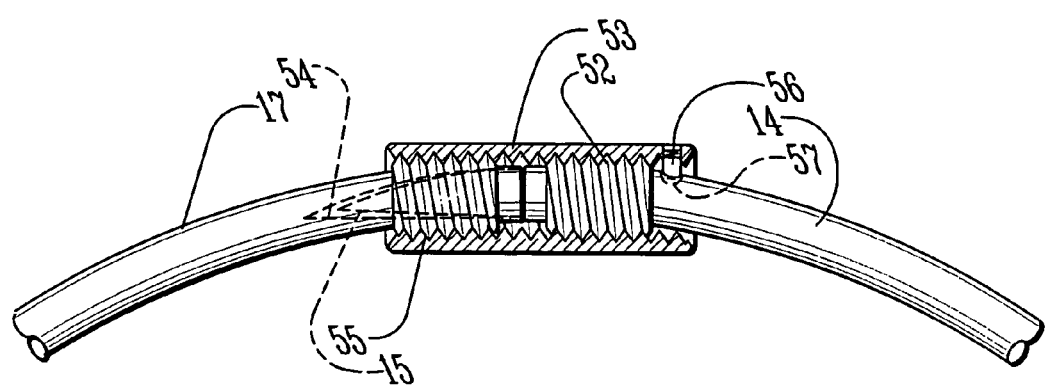
FIG. 11B is a side elevation view of the embodiment of FIG. 11A in the locked position.

A still further alternative embodiment may be described with respect to FIGS. 11A-B. This embodiment is similar to that of FIGS. 10A-C with the addition of a spring loaded ball 56 associated with the lock portion 17 and a complementary socket 57 on the needle portion 14. (The spring is not shown.) The spring loaded ball 56 is disposed on the interior of the protective cap 53. As in the previously described embodiment of FIGS. 10A-C, in order to protect the tip 15 and to lock the needle portion 14 to the lock portion 17, the tip 15 is placed within the complementary hollow 54 and the protective cap 53 is threadedly advanced over the threaded sections 55, 52 of the needle portion 14 and the lock portion 17 as shown in FIG. 11C. When the spring loaded ball 56 is advanced along with the protective cap 53 to the point where it is disposed adjacent to the complementary socket 57, the spring loaded ball 56 falls into the socket 57 and thus serves to further secure the needle portion 14 to the lock portion 17.

Figure 12:
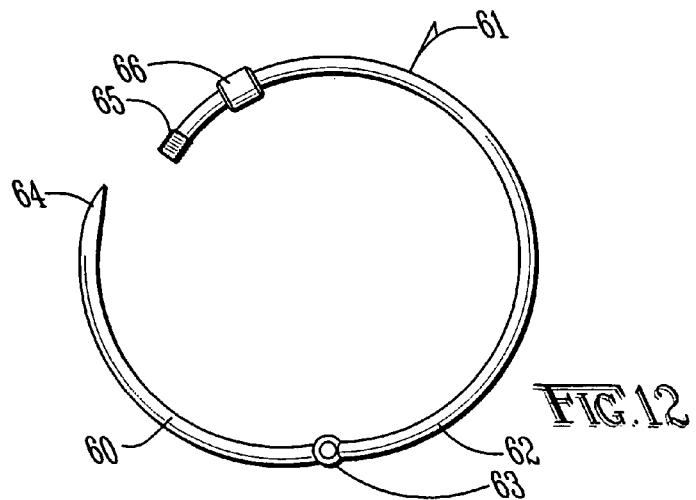
FIGS. 12-14 are elevation views of an additional alternative embodiment of the closure device of the present invention where the needle portion comprises a circular arc of approximately ⅜ of the circular circumference and the lock portion comprises a circular arc of approximately ⅝ of the circular circumference.
Figure 13:
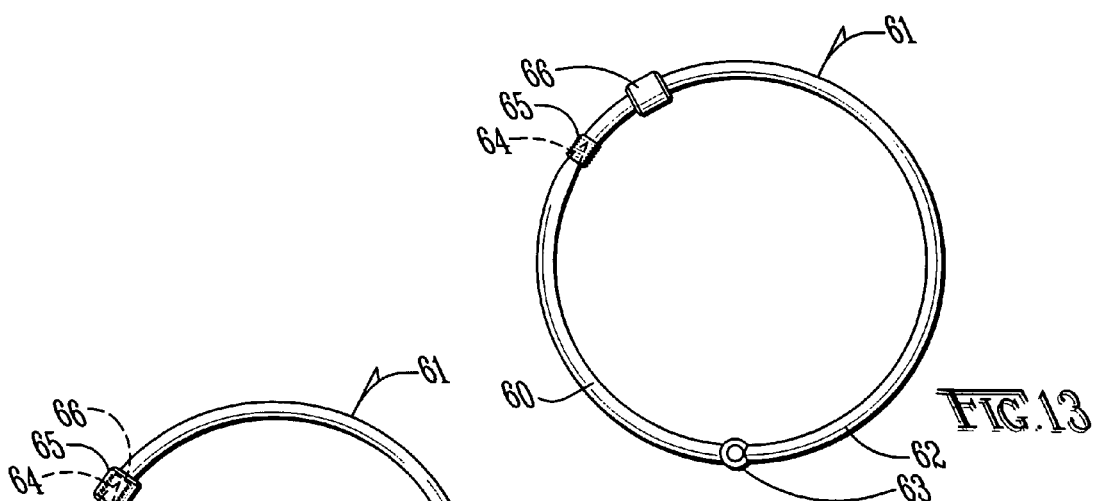
Figure 14:
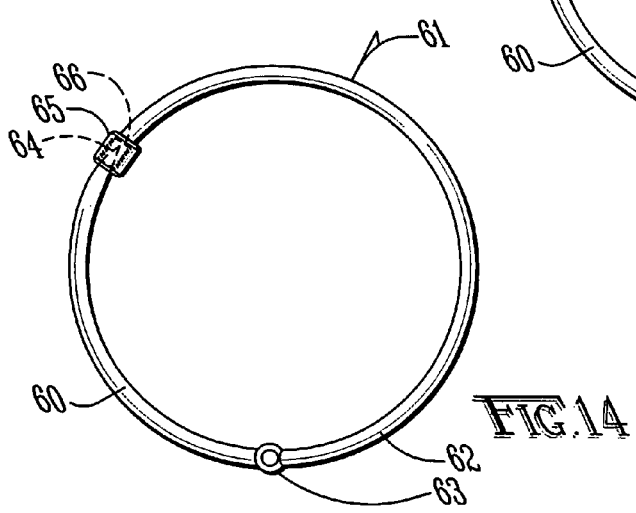

As noted above, angling the needle tip with respect to the protective cap, allows the protective cap to lock the needle portion with respect to the lock portion. If the needle portion and the lock portion are in the shape of circular arcs, the appropriate angle may be obtained if the needle portion describes less than ½ of the circular circumference and the lock portion describes greater than ½ of the circular circumference. FIGS. 12-14 are elevation views of an additional alternative embodiment of the closure device of the present invention where the needle portion 60 comprises a circular arc of approximately ⅜ of the circular circumference of the entire needled carabiner 61 and the lock portion 62 comprises a circular arc of approximately ⅝ of the circular circumference of the needled carabiner 61. The needle portion 60 and the lock portion 62 are connected together at respective first ends by a hinge 63. The needle tip 64 thus rotates along a circular arc that is smaller in radius than the radius of the entire needled carabiner 61. Therefore, when the needle portion 60 is rotated away from the lock portion 62, it moves outwardly rather than along a tangent as would occur if the needle portion 60 and the lock portion 62 were equal circular arcs. Thus, a protective cap 65 placed over the needle tip 64 effectively locks the needle portion 60 to the lock portion 62.

A screw tip 66 is disposed on a second end of the lock portion 62 to receive the needle tip, which is disposed on a second end of the needle portion 60, the respective second ends being disposed oppositely to the respective first ends. As shown in FIGS. 15 and 16, the screw tip 66 is provided with a recess 67 which is shaped and angled to provide a complementary space to securely received the needle tip 64.

FIG. 12 shows the needled carabiner 61 in the open position, while FIG. 13 shows the needle tip 64 received into the recess 67 of the screw tip 66. The screw tip 66 is provided with external screw threads for threadedly receiving the protective cap 65 which is provided with complementary internal screw threads. After the needle tip 64 is received into the recess 67, the protective cap 66, as shown in FIGS. 14 and 17 is screwed over the needle tip 66 to lock the needle portion 60 to the lock portion 62.

The present invention has been described with reference to certain preferred and alternative embodiments that are intended to be exemplary only and not limiting to the full scope of the present invention as set forth in the appended claims. For example, various other forms of securing elements known to those of skill in the art are contemplated as being within the scope of the present invention.

What is claimed is:

1. A physiologic abdominal closure device, comprising:
 a first needled carabiner, wherein said first needled carabiner comprises a needle portion having a first end and a needle tip at a second end, a lock portion having a first end and a second end, said first end of said lock portion connected to said first end of said needle portion by a hinge, wherein said hinge is a pivot point, and a securing element associated with said second end of said lock portion wherein said needle tip of said first needled carabiner is configured to pierce a first portion of a tissue of a subject, wherein said second end of said lock portion is configured to engage said needle tip, wherein said securing element comprises a protective cap configured to prevent said needle tip and second second end of said lock portion from disengaging, wherein said protective cap is slidably received on said lock portion of said first needled carabiner;
 a second needled carabiner, wherein said second needled carabiner comprises a needled portion having a first end and a needle tip at a second end, a lock portion having a first end and a second end, said first end of said lock portion connected to said first end of said needle portion by a hinge, wherein said hinge is a pivot point wherein said needle tip of said second needled carabiner is configured to pierce a second portion of said tissue of said subject; and
 a tensioner having a first end and a second end, wherein said first end of said tensioner is fastened to said lock portion of said first needled carabiner and said second end of said tensioner is fastened to said lock portion of said second needled carabiner, wherein said tensioner is expandable and contractable wherein said tensioner is configured to control a distance between said first portion of said tissue and said second portion of said tissue of said subject.

2. The closure device of claim 1 wherein said
 protective cap internal threads wherein said securing element further comprises
 a screw having external threads and further having a hollow for receiving said needle tip, said screw disposed on said second end of said lock portion of said first needled carabiner for threadedly receiving said cap.

3. The closure device of claim 2, wherein said needle portion comprises a circular arc of less than ½ of a circular circumference and said lock portion comprises a circular arc greater than ½ of a circular circumference.

4. The closure device of claim 1, wherein said tensioner comprises a rubber band.

5. The closure device of claim 1, wherein said tensioner comprises a spring.

6. The closure device of claim 1 wherein said securing element comprises:
 a recess on said needle portion; and
 a complementary recess on said lock portion for interlocking with said recess.

7. The closure device of claim 1, wherein said first needled carabiner and said second needled carabiner are round.

* * * * *